US00PP36571P3

(12) United States Plant Patent
Chengquian

(10) Patent No.: US PP36,571 P3
(45) Date of Patent: Mar. 25, 2025

(54) ***PHILODENDRON* PLANT NAMED 'GUOQIAN'**

(50) Latin Name: *Philodendron tatei*
Varietal Denomination: GUOQIAN

(71) Applicant: Qui Chengquian, Foshan (CN)

(72) Inventor: Qui Chengquian, Foshan (CN)

( * ) Notice: Subject to any disclaimer, the term of this patent is extended or adjusted under 35 U.S.C. 154(b) by 0 days.

(21) Appl. No.: 18/831,084

(22) Filed: Jun. 24, 2024

(65) Prior Publication Data

US 2025/0008855 P1 Jan. 2, 2025

(30) Foreign Application Priority Data

Jun. 27, 2023 (QZ) ..... PBR 2023/1419

(51) Int. Cl.
*A01H 5/12* (2018.01)
*A01H 6/10* (2018.01)

(52) U.S. Cl.
USPC ..... Plt./381
CPC ..... *A01H 6/10* (2018.05)

(58) Field of Classification Search
USPC ..... Plt./381
CPC ..... A01H 5/12; A01H 5/00; A01H 6/10
See application file for complete search history.

(56) References Cited

U.S. PATENT DOCUMENTS

PP6,337 P * 10/1988 DeCoster ..... Plt./381

OTHER PUBLICATIONS

Lanoue 2024, Cafe Planta How fast do *Philodendron* grow: A comprehensive guide, retrieved on Oct. 1, 2024 at https://cafeplanta.com/a/blog/how-fast-do-philodendron-grow-a-comprehensive-guide, 10 pp. (Year: 2024).*

* cited by examiner

*Primary Examiner* — June Hwu
(74) *Attorney, Agent, or Firm* — Samuel R. McCoy, Jr.

(57) ABSTRACT

'GUOQIAN' is a new and distinctive *Philodendron tatei* plant which is characterized by the combination of a relatively large stature, large glossy foliage borne on prominent red petioles, juvenile foliage that is colored with a mixture of yellow-green and greyed-brown on the upper surface and greyed-orange with yellow-green suffusion on the lower surface, mature foliage that is colored dark green on the upper surface and yellow-green with greyed-orange suffusion on the lower surface, and the stability of all characteristics from generation to generation.

3 Drawing Sheets

Latin name of the genus and species: The Latin name of the genus and species of the novel variety disclosed herein is *Philodendron tatei.*

Variety denomination: The inventive variety of *Philodendron* disclosed herein has been given the variety denomination 'GUOQIAN'.

BACKGROUND OF THE INVENTION

Parentage: 'GUOQIAN' is a spontaneous whole-plant mutation which was discovered growing amongst a cultivated population of greenhouse-grown *Philodendron tatei* 'Rojo Congo' plants (U.S. Plant Pat. No. 14,116) which was first observed by the inventor in 2018 at a commercial nursery in the Panyu district of Guangzhou, China. The mutation was first noted for its uniquely-colored leaves relative to those of the parent plant and was subsequently isolated for further evaluation in order to confirm the distinctness and stability of the characteristics first observed. From 2018 through 2022, the claimed plant was evaluated against other comparators, at multiple secure and confidential sites. Upon confirmation of distinctness and stability, the new *Philodendron* plant was selected for commercialization and given the name 'GUOQIAN'.

Asexual Reproduction: Asexual reproduction of the new cultivar 'GUOQIAN', by way of vegetative division, was first initiated in 2019, at a nursery in Foshan, China. Through twelve subsequent generations, the unique features of this cultivar have proven to be stable and true to type.

SUMMARY OF THE INVENTION

The cultivar 'GUOQIAN' has not been observed under all possible environmental, conditions. The phenotype may vary somewhat with variations in environment such as temperature, day length, and light intensity, without, however, any variance in genotype. The following traits have been repeatedly observed and are determined to be the unique characteristics of 'GUOQIAN'. These characteristics in combination distinguish 'GUOQIAN' as a new and distinct *Philodendron* cultivar:

1. *Philodendron* 'GUOQIAN' exhibits a relatively large plant size with large, glossy foliage; and
2. *Philodendron* 'GUOQIAN' exhibits juvenile foliage that is colored with a mixture of yellow-green and greyed-brown adaxially, and greyed-orange with yellow-green suffusion, abaxially; and
3. *Philodendron* 'GUOQIAN' exhibits mature foliage that is colored dark green adaxially, and yellow-green with greyed-orange suffusion abaxially; and
4. *Philodendron* 'GUOQIAN' exhibits dark greyed-orange to greyed-red petioles, which generally appear red.

BOTANICAL DESCRIPTION OF THE PLANT

Figure 1:
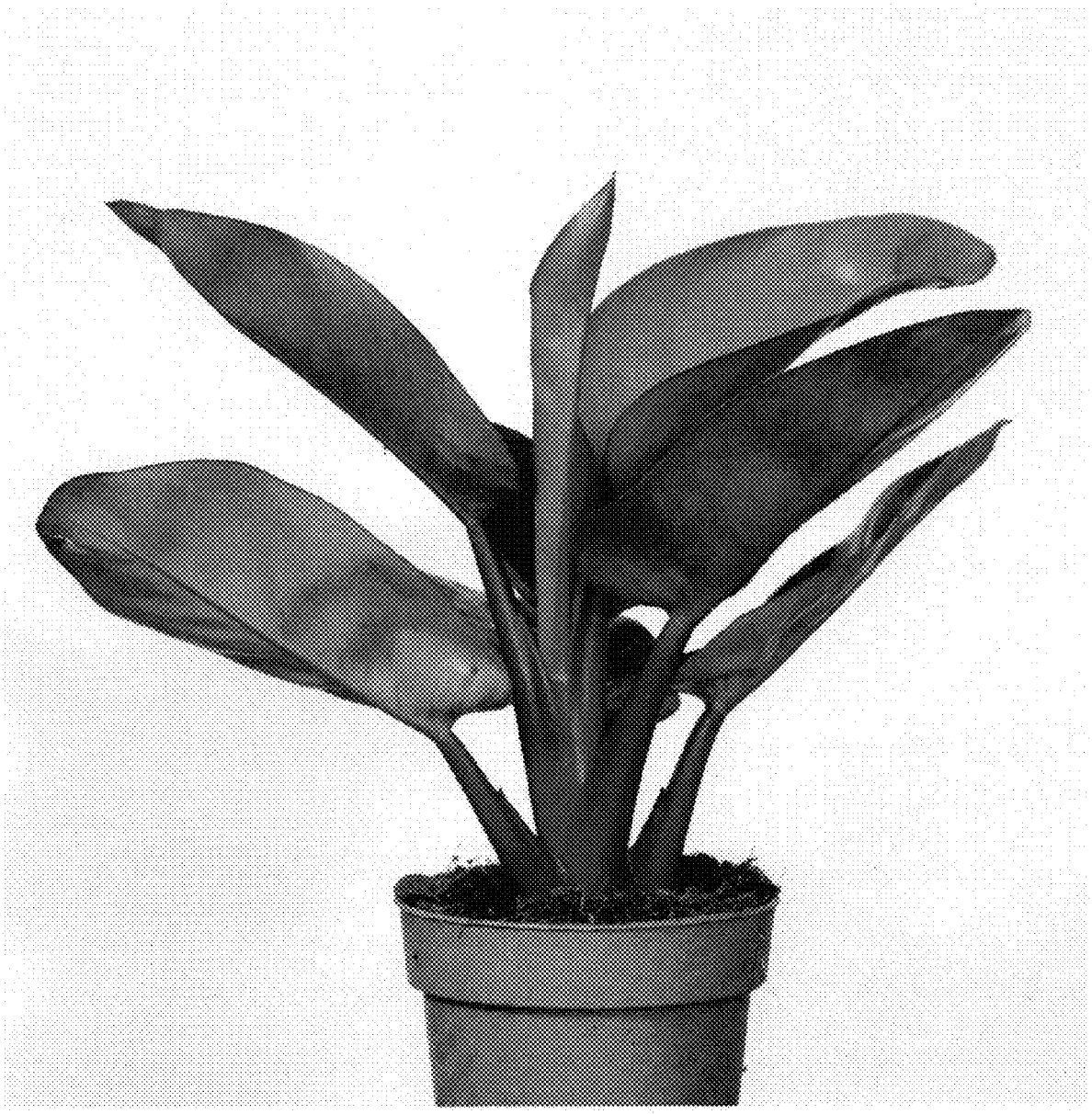
FIG. 1 illustrates, as nearly true as it is reasonably possible to make the same in color photographs of this type, an exemplary plant of 'GUOQIAN' grown in a commercial plant nursery in Guangzhou, China. This plant is approximately 12 months old in a 13 cm container.
Figure 2:
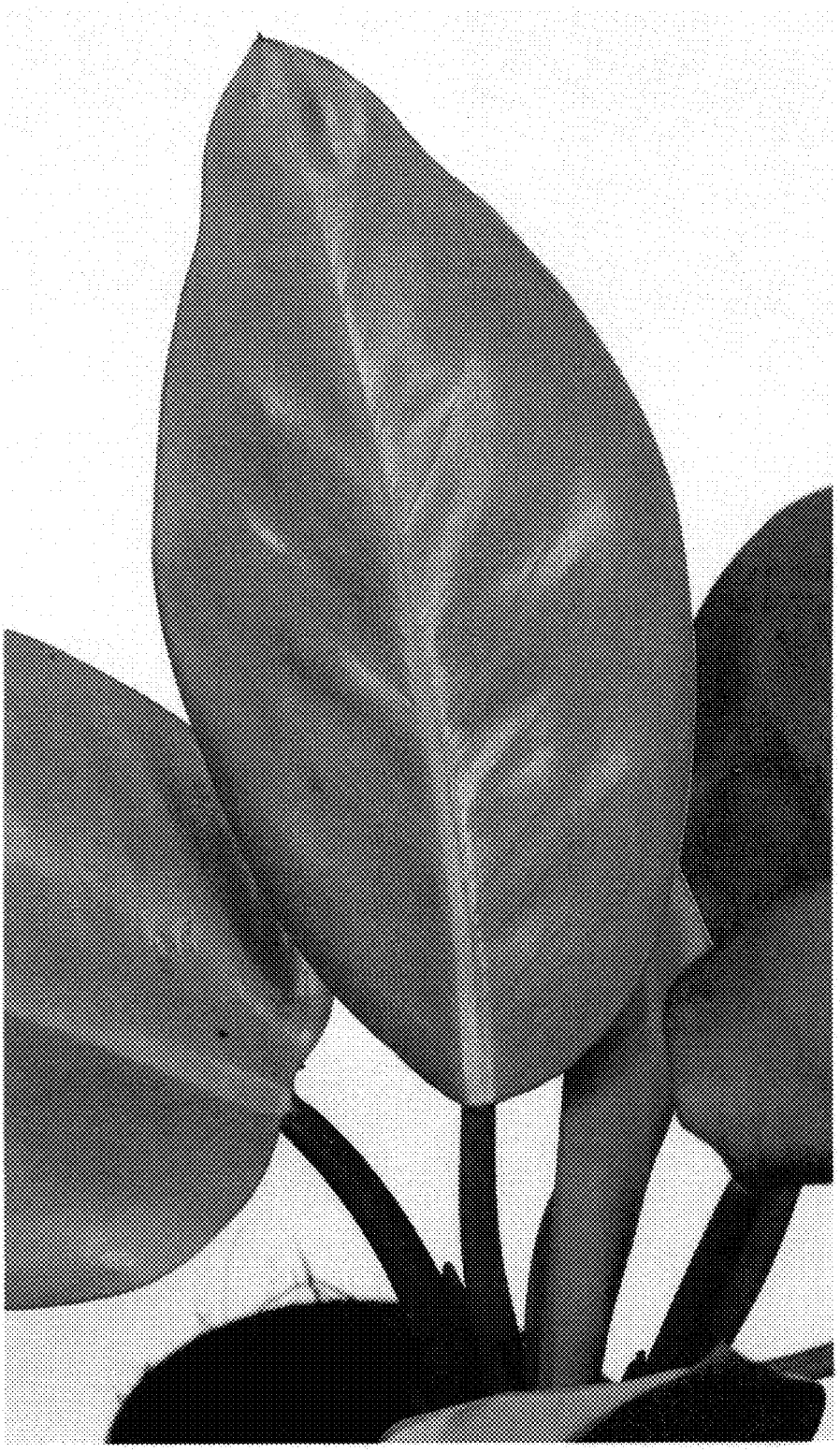
FIG. 2 illustrates, as nearly true as it is reasonably possible to make the same in color photographs of this type, the adaxial surface of the juvenile foliage of 'GUOQIAN'.
Figure 3:
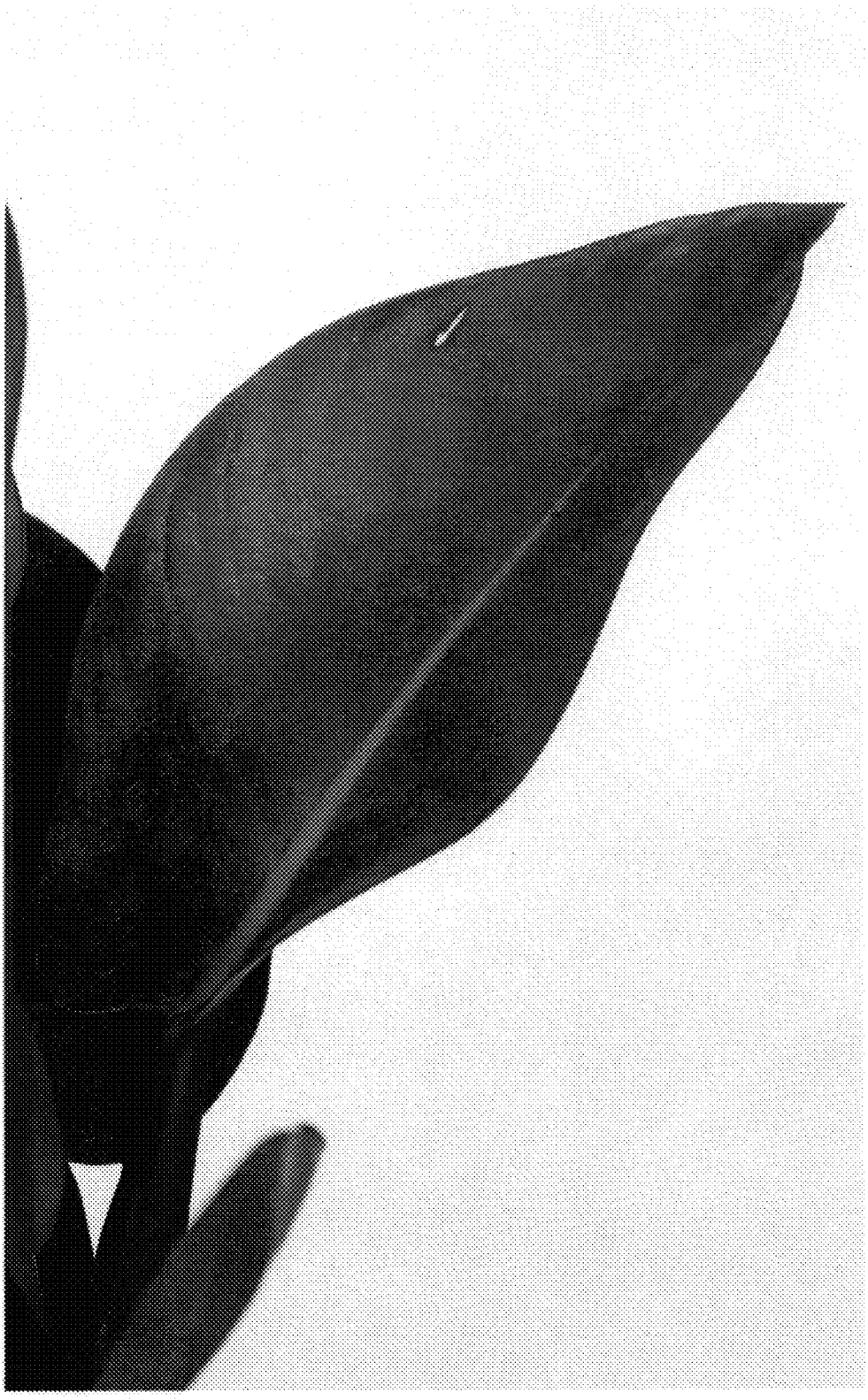
FIG. 3 illustrates, as nearly true as it is reasonably possible to make the same in color photographs of this type, the adaxial surface of the mature foliage of 'GUOQIAN'.

The following observations and measurements, made in November of 2023, describe averages from a 12-month-old 'GUOQIAN' plant grown in 13 cm nursery containers at a commercial plant nursery in Guangzhou, China. Plants were produced using conventional production protocols for *Philodendron* sp. which consisted of growing plants under shade cloth, regular overhead irrigation, supplemental fertilizer as needed, and chemical pest measures to control both disease and insect pests.

Those skilled in the art will appreciate that certain characteristics will vary with older or, conversely, with younger plants. 'GUOQIAN' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'GUOQIAN' and a comparison with the parent plant and most similar commercial cultivar are provided below.

Plant description:

*Growth habit*.—Broad-spreading to upright monopodial perennial with basal foliage. Plants will develop a short, unbranched stem with age.

*Plant profile shape*.—Flattened globular.

*Height from soil level to top of foliar plane*.—26.8 cm.

*Plant spread*.—39.2 cm.

*Number of basal shoots per plant*.—1.

*Propagation*.—Type — Asexual propagation is accomplished by way of stem and leaf cuttings which root well without rooting compound or hormone. Time to initiate rooting — Approximately 25 days at 28 degrees Celsius. Time to produce a rooted cutting — Approximately 6 to 8 months are needed to produce a marketable plant in a 13 cm container.

*Disease and pest resistance or susceptibility*.—Neither susceptibility nor resistance to pests and diseases common to either *Philodendron* have been observed.

*Environmental tolerances*.—Adapt to temperatures as low as 5 degrees Celsius and at least as high as 40 degrees Celsius; moderate tolerance to rain; low to moderate tolerance to wind.

Stems:

*Branching characteristics*.—*Philodendron* sp. is a monopodial plant; plants eventually develop a stem with age.

*Attitude*.—Varying from 30 to 90 degrees from horizontal.

*Aspect*.—Terete.

*Length*.—Approximately 5.5 cm.

*Width*.—Approximately 1.8 cm.

*Internode length*.—Approximately 0.9 cm.

*Strength*.—Strong.

*Texture*.—Glabrous.

*Luster*.—Moderately glossy.

*Color*.—Greyed-purple, nearest to RHS 185A; greyed-purple, RHS 187B, at the nodes.

Foliage:

*Quantity*.—9 leaves per shoot.

*Arrangement*.—Alternate.

*Attachment*.—Petiolate.

*Division*.—Simple.

*Lamina*.—Shape — Ovate. Length — 19.1 cm, excluding the petiole. Width — 11.9 cm. Apex — Apiculate. Base — Cordate to truncate. Aspect — Flat to slightly concave. Margins — Entire; slightly coarsely undulated to not undulated. Texture and luster, adaxial surface — Smooth, glabrous and slightly glossy. Texture and luster, abaxial surface — Smooth, glabrous and slightly glossy. Color- Juvenile foliage, adaxial surface — Nearest to a mixture of yellow-green to greyed-brown, RHS 152D and 199D, and lightly to moderately suffused with yellow-green towards the central zone, nearest to RHS 146C; the laminas are further suffused with greyed-orange, nearest to RHS 174C; narrowly margined greyed-purple, nearest to RHS 183A. Juvenile foliage, abaxial surface — Greyed-orange, nearest to a combination of RHS 174B and 174C, and suffused with yellow-green towards the central zone, nearest to RHS 153A; narrowly margined greyed-purple, nearest to RHS 184A. Mature foliage, adaxial surface — Green, nearest to a mixture of RHS 137A and 141A yet slightly darker; narrowly margined greyed-red, nearest to RHS 182B. Mature foliage, abaxial surface — Yellow-green, nearest to a mixture of RHS 144A and 146C, and lightly suffused with greyed-orange, nearest to a combination of RHS 177B and 177C; narrowly margined greyed-purple, nearest to a combination of RHS 183A and 183B.

*Venation*.—Pattern — Pinnate. Color — Juvenile foliage, adaxial surface — Main vein is greyed-orange, nearest to RHS 177C; all other veins are a darker shade of greyed-orange, nearest to RHS 176A. Juvenile foliage, abaxial surface — Greyed-orange, nearest to RHS 176A. Mature foliage, adaxial surface — Yellow-green, nearest to RHS 144A. Mature foliage, abaxial surface — Greyed-orange, nearest to RHS 176A.

*Petiole*.—Attitude — Upright and outward. Strength — Moderately strong. Aspect — Subterete. Length — 13.7 cm. Height — 1.1 cm. Width — 1.4 cm. Texture and luster, adaxial surface — Smooth, glabrous and slightly glossy. Texture and luster, abaxial surface — Smooth, glabrous and slightly glossy. Color, adaxial surface — Greyed-orange, nearest to a combination of RHS 176A and 176B, and blotched with greyed-orange, nearest to RHS 177B; fading to greyed-red proximally, nearest to RHS 181A. Color, abaxial surface — Greyed-orange, nearest to RHS 176A, and blotched with greyed-red, nearest to RHS 178B; fading to greyed-red proximally, nearest to a combination of RHS 180A and 181A. Petiole Wings — Position-Proximal end of the petiole. Length — 10.3 cm. Width — 0.5 cm. Color, adaxial surface — Greyed-red, nearest to RHS 181A. Color, abaxial surface — Greyed-red, nearest to RHS 178A yet darker.

Inflorescence: To date, 'GUOQIAN' has not flowered.

COMPARISONS WITH THE PARENT PLANTS

Plants of the new cultivar 'GUOQIAN' differ from the parent, *Philodendron tatei* 'Rojo Congo', in the characteristics described in Table 1 below.

TABLE 1

| Characteristic | 'GUOQIAN' | 'Rojo Congo' |
|---|---|---|
| General coloration of the juvenile foliage. | A mixture of yellow-green and greyed-brown with greyed-orange suffusion, adaxially, and greyed-orange with yellow-green suffusion, abaxially. | Green adaxially and yellow-green with light greyed-orange suffusion, abaxially. |
| General coloration of the mature foliage. | Dark green adaxially, and yellow-green with strong grey-orange suffusion abaxially | Dark green adaxially, and yellow-green abaxially; abaxial surface occasional lightly suffused with greyed-orange. |

TABLE 1-continued

| Characteristic | 'GUOQIAN' | 'Rojo Congo' |
|---|---|---|
| General coloration of the petiole. | Red. | A mixture of dark purple and brown. |

COMPARISONS WITH THE MOST SIMILAR COMMERCIAL VARIETY

Plants of the new cultivar 'GUOQIAN' differ from the parent, *Philodendron tatei* 'Imperial Red' (U.S. Plant Pat. No. 6,337), in the characteristics described in, Table 2 below.

TABLE 2

| Characteristic | 'QUOQIAN' | 'Imperial Red' |
|---|---|---|
| General coloration of the juvenile foliage. | A mixture of yellow-green and greyed-brown with greyed-orange suffusion, adaxially, and greyed-orange with yellow-green suffusion, abaxially. | Dark maroon, adaxially, and light maroon, abaxially. |
| General coloration of the mature foliage. | Dark green, adaxially, and yellow-green with greyed-orange suffusion, abaxially | Very dark green with maroon suffusion, adaxially, and green with light maroon suffusion, abaxially. |
| General coloration of the petiole. | Red. | Dark yellow-green with greyed-red suffusion. |

Which is claimed is:

1. A new and distinct variety of *Philodendron tatei* plant named 'GUOQIAN', substantially as described and illustrated herein.

* * * * *